(12) United States Patent
Pola

(10) Patent No.: US 7,728,037 B2
(45) Date of Patent: Jun. 1, 2010

(54) ALPHA-KETOGLUTARATES OF ACTIVE INGREDIENTS AND COMPOSITIONS CONTAINING SAME

(75) Inventor: Pietro Pola, Rocca di Papa (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 926 days.

(21) Appl. No.: 11/443,458

(22) Filed: May 31, 2006

(65) Prior Publication Data

US 2006/0241181 A1  Oct. 26, 2006

Related U.S. Application Data

(63) Continuation-in-part of application No. 10/484,927, filed as application No. PCT/IT01/00549 on Oct. 29, 2001, now abandoned.

(30) Foreign Application Priority Data

Jul. 25, 2001  (IT) .......................... RM2001A0445

(51) Int. Cl.
  *A61K 31/22*  (2006.01)
  *C07C 229/06*  (2006.01)
(52) U.S. Cl. .......................... 514/561; 424/72; 560/155
(58) Field of Classification Search ................ 560/155; 514/561; 424/72
See application file for complete search history.

(56) References Cited

U.S. PATENT DOCUMENTS

| 4,602,039 A | 7/1986 | Cavazza ...................... 514/561 |
| 4,883,786 A * | 11/1989 | Puricelli ...................... 514/47 |
| 5,073,376 A | 12/1991 | Kohl et al. .................. 424/451 |
| 5,270,297 A | 12/1993 | Paul et al. ...................... 514/23 |
| 5,292,538 A | 3/1994 | Paul et al. ...................... 426/74 |
| 5,817,329 A | 10/1998 | Gardiner ...................... 424/439 |

FOREIGN PATENT DOCUMENTS

DE  199 29 993 A  1/2001

OTHER PUBLICATIONS

Berge et al. "Pharmaceutical salts" J. Pharm. Sci. 66(1) p. 1-19 (1977).*
Guarnieri et al, "Carnitine metabolism in uremia" CA 136:276784 (2001).
Jordaan et al, "Pharmaceuticals and nutritional . . . " CA 142:379275 (2004).
Mountcastle "Medical Physiology" Mosbey Co., p. 847-848 (1968).

* cited by examiner

*Primary Examiner*—Celia Chang
(74) *Attorney, Agent, or Firm*—Lucas & Mercanti, LLP

(57) ABSTRACT

Novel stable and pharmacologically acceptable salts of L-carnitine and lower alkanoyl L-carnitines with alpha-ketoglutaric acid are disclosed as well as the compositions useful as dietary and dietetic supplements, nutraceuticals or drugs containing same.

9 Claims, No Drawings

ALPHA-KETOGLUTARATES OF ACTIVE INGREDIENTS AND COMPOSITIONS CONTAINING SAME

This application is a continuation-in-part of application Ser. No. 10/484,927, filed Apr. 7, 2004, which in turn is a U.S. phase of PCT/IT01/00549 filed Oct. 29, 2001 which claims priority of IT RM2001A000445 filed Jul. 25, 2001, the entire content of each of which is hereby incorporated by reference in this application.

The present invention relates to novel, stable and pharmacologically acceptable salts of L-carnitine and lower alkanoyl L-carnitines which favourably lend themselves to the preparation of orally, parenterally or sublingually administrable compositions which can be both solid or, thanks to the salt water solubility, liquid as well. The compositions are useful in the field of dietary and dietetic supplements, health foods, and nutraceutical in addition to the strict pharmaceutical field.

The invention also relates to the compositions thus obtained.

It has long since been known that L-carnitine and lower L-carnitines lend themselves to various therapeutic utilizations.

For instance, L-carnitine is used in the cardiovascular field as a support drug for the treatment of acute and chronic myocardial ischaemia, angina pectoris, heart failure and cardiac arrhythmias.

In the nephrological field, L-carnitine is administered to chronic uraemics undergoing regular haemodialytic treatment to combat myasthenia and the onset of muscular cramps.

Acetyl L-carnitine is used in the neurologic field for the treatment of both central nervous system disturbances and peripheral neuropathies, particularly diabetic peripheral neuropathy. Propionyl L-carnitine is used for the treatment of chronic arteriosclerosis obliterans, particularly in patients showing the symptom of severely disabling intermittent claudication.

Herehinbelow, reference shall be exclusively made, for simplicity's sake, to L-carnitine, it being understood, however, that all disclosures apply to the lower alkanoyl L-carnitines as well.

A widespread promotion of carnitine and derivatives thereof has rapidly been taking place towards utilizations other than those purely therapeutical, ever though allied to them.

It has, in fact, been widely recognized that in professional athletes as well as in any subject practising sport at amateur level, L-carnitine supplies energy to the skeletal musculature and increases the resistance to prolonged, intense stress, enhancing the performance capability of such individuals.

In addition, L(−)-carnitine or its lower alkanoyl derivatives constitute indispensable nutritional supplements for both vegetarians, whose diet have a low carnitine content as well as a low content of the two amino acids, lysine and methionine (the precursors of the biosynthesis of L(−)-carnitine in the kidneys and liver) and for those subjects who have to live on a diet poor in protein for prolonged periods of time.

Consequently, various compositions containing L-carnitine alone or in combination with other active ingredients (see e.g. the combination composition carnitine/coenzyme $Q_{10}$) have recently reached the market of the health foods, dietary supplements, energy foods and similar products, i.e. those compositions which sold as OTCs are not addressed to purely therapeutic purposes, but are aimed to the well-being and at producing a general improvement in fitness and performances on the part of the consumer and which have recently termed "nutraceuticals".

Of growing interest, moreover, is the use of L(−)-carnitine in the veterinary field and as animal feed supplements in the breeding of valuable animals such as racehorses and thoroughbreds.

In all the aforesaid both "ethical" and "non ethical" applications, L-carnitine is not generally used in the form of its inner salt, owing to the extremely high hygroscopicity thereof.

Indeed, L-carnitine inner salt's hygroscopicity brings about complex problems of processing, stability and storage both of the raw materials and of the finished products. For example, L(−)-carnitine tablets have to be packaged in blisters to keep them out of contact with the air, since, otherwise, even in the presence of normal humidity conditions, they would undergo alterations, swelling up and becoming pasty and sticky. Moreover, owing to the inadequate stability, traces of trimethylamine are released which give the products as unpleasant fishy odour.

The problem of the hygroscopicity of L-carnitine inner salt has substantially been solved by converting it to salts of "pharmacologically acceptable acids" on the assumption that these salts maintain the same therapeutic/nutritional activities as those of the inner salt and do not present unwanted toxic or side effects.

As known, alpha-ketoglutaric acid plays an important metabolic role, which is correlated to that played by L-carnitine.

For instance, in phenylketokuria carnitine synthesis is hindered and the resulting decrease is correlated to the lowering of alpha-ketoglutaric acid concentration, whose presence is critical for restoring carnitine basal values insofar as it acts as coenzyme of butyrobetaine hydroxylase.

It is, furthermore, known the glutamine role in maintaining muscle functional capacity and that a glutamine decrease can be detected in several pathological conditions or muscular stress. Since alpha-ketoglutaric acid is a glutamine precursor, its administration was shown to improve a number of muscle pathologies such as those occurring in muscular injuries.

Alpha-ketoglutarate administration has been also successfully adopted in cardiac surgery owing to the important role played by alpha-ketoglutaric acid in the Krebs cycle and, hence, in myocardial metabolism. Consequently, its use as cardioprotective agent has been suggested. Since alpha-ketoglutaric acid can act as mitochondrial carrier, just as carnitine does, and can, therefore, similarly to carnitine, correct some so-called mitochondriocytopathies, its favourable metabolic effects not only at the cardiac level but also at the level of other organs such as the renal tract can be accounted for.

Moreover, in uremics undergoing regular haemodialytic treatment calcium ketoglutarate was shown to be effective in preventing hyperphosphataemia.

There is now an extensive body of literature, particularly patents, disclosing the production of stable, non-hygroscopic salts of L(−)-carnitine.

With specific reference to the two only salts which have been actually marketed to-date as nutritional supplements, U.S. Pat. No. 4,602,039 (Sigma-Tau) discloses L(−)-carnitine acid fumarate (1:1) as a non-hygroscopic, pharmacologically acceptable L(−)-carnitine salt. EP 0 434 088 (Lonza) discloses the use of L(−)-carnitine tartrate (2:1), the preparation and physico-chemical characterization of which were, on the other hand, already described by D. Müller and E. Strack in Hoppe Seyler's Z. Physiol. Chem. 353, 618-622, April 1972, for the preparation of solid forms suitable for the oral administration, such as tablets, capsules, powders or granulates, as said salts are capable of resisting at about 60% relative humidity.

The solution of the purely technological problem of hygroscopicity of L-carnitine inner salt has confined so far to the background the consideration of more substantial pharmacological aspects, such as the finding of L-carnitine salts, whose anion moiety itself be endowed with interesting pharmacological characteristics and, furthermore, be apt to enhance, if possible in a synergic way, the therapeutical and/or nutritional properties of L-carnitine inner salt.

The object of the present invention is to provide such novel, stable pharmacologically acceptable salts of L-carnitine and lower alkanoyl L-carnitines which not only possess an enhanced therapeutical and/or nutritional efficacy with respect to the corresponding inner salts, but also, owing to their water solubility, are more easily absorbable resulting in higher haematic concentration of L-carnitine in shorter times with respect to those achievable with L-carnitine inner salt or its pharmacologically acceptable salts known to-date.

According to the invention, the aforesaid object is achieved via the L-carnitine and lower alkanoyl L-carnitines alpha-ketoglutarates having the formula:

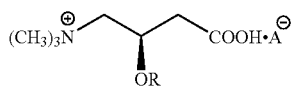

wherein:

A⁻ is the alpha-ketoglutarate anion; and

R is hydrogen or a straight- or branched-chain lower alkanoyl having 2-5 carbon atoms.

When R is alkanoyl, it is preferably selected from the group consisting of acetyl, propionyl, valeryl and isovaleryl.

Particularly preferred alpha-ketoglutarates of the invention are the following:

L-carnitine alpha-ketoglutarate;

acetyl L-carnitine alpha-ketoglutarate;

propionyl L-carnitine alpha-ketoglutarate;

valeryl L-carnitine alpha-ketoglutarate; and isovaleryl L-carnitine alpha-ketoglutarate.

The alpha-ketoglutarate of the invention presents the favourable metabolic properties of both L-carnitine or alkanoyl L-carnitine and alpha-ketoglutaric acid with a synergistic effect.

Example of Preparation of L-carnitine Alpha-ketoglutarate 0.1 moles of L-carnitine inner salt (16.2 g) were dissolved in distilled water (200 mL). 0.1 moles of alpha-ketoglutaric acid (16.6 g) were added under stirring to the solution. The addition was carried out portionwise taking care that, when the addition was over, the solution remained clear.

The excess of water was evaporated under reduced pressure until a thick honey-like pasty mass was obtained composed of the hydrated form of L-carnitine alpha-ketoglutarate. The salt, whose molecular weight is 389, was completely water soluble at 25° C. Its IR spectrum was consistent with the salt structure of the compound.

Preparation of Solid Compositions

EXAMPLE 1

15.2 g of L-carnitine inner salt, 16.6 g of alpha-ketoglutaric acid, 2 g of METHOCEL E50L and 70 g of glucose were dissolved in 300 mL of distilled water.

The resulting solution was filtered, the filtrate brought to −40° C. and lyophilized.

112 g of a flowable cream-colored powder which remained unchanged over time, were obtained.

EXAMPLE 2

The procedures of Example 1 were repeated, substituting mannitol for glucose.

EXAMPLE 3

The procedures of Example 1 were repeated, substituting lactose for glucose.

EXAMPLE 4

The procedures of Example 1 were repeated, substituting fructose for glucose.

The product obtained simply by water evaporation can be manufactured as capsules which rapidly dissolve when placed under the tongue or in the oral cavity.

As an alternate route, L-carnitine alpha-ketoglutarate can be stabilized by adding thereto glucose, fructose, lactose or mannitol or other sugars, as shown in Examples 1-4.

In this case, L-carnitine alpha-ketoglutarate spreads evenly, infact, on the solid base consisting of lactose, fructose, glucose or mannitol, resulting in a well preservable powder.

As apparent to any expert in pharmaceutical technology, the end product can be supplemented with stabilizers and preservatives currently used in pharmaceutical preparations or dietary/nutritional supplements, or with other active ingredients selected from drugs, nutrients and dietetic agents such as vitamins, amino acids, mineral salts or products of vegetable origin.

Further additional substances comprise binders, lubricants, mold-release agents, flow-regulating agents, dispersing agents, colorants and flavoring agents.

Absorption Tests on L-carnitine Alpha-ketoglutarate

For these tests a batch of male Sprague Dawley rats with a mean body weight of 250 g was used. After fasting for 24 hours, the rats were divided into three groups which were administered orally 1 g/kg of L-carnitine alpha-ketoglutarate and equimolar doses of L-carnitine and alpha-ketoglutaric acid, respectively. The L-carnitine assay was conducted on blood samples taken from the animals 1, 2 and 4 hours after administration using the spectrophotometric method described by Schafer (Schafer Y., Reichmann E., Clin. Chim., Acta, 182, 87, 1989).

The results of these tests demonstrate that L-carnitine alpha-ketoglutarate is well absorbed and yields higher blood concentrations in shorter periods of time than those achieved after administration of equivalent doses of L-carnitine. Whereas, in fact, with L-carnitine alpha-ketoglutarate the L-carnitine concentrations reached their peak after as little as 1 hour (166.5±20.1 nmol/l), with the administration of equimolecular doses of L-carnitine, the peak concentration was obtained only after 2 hours (128.8±18.8 nmol/l) and was in any case lower than that obtainable with L-carnitine alpha-ketoglutarate.

Metabolic Tests

For the purposes of demonstrating the favourable metabolic action of the new compound, tests were conducted on rabbit heart papillary muscle subjected to hypoxia, evaluating the reduction in ATP energy reserves after treatment with L-carnitine alpha-ketoglutarate (1 g/kg by mouth) or with equimolecular doses of L-carnitine or alpha-ketoglutaric acid or combination of these.

After three consecutive days of treatment, sections of papillary muscle were isolated from the rabbit hearts and were perfused in a thermostatized bath with a saturated solution of 100% $O_2$. On replacing the $O_2$ in the bath with 100% Na, a condition of hypoxia was induced which caused a reduction in ATP concentrations in the muscle.

ATP concentrations were monitored according to the method described by Strehler (Strehler B. L., Methods in Enzymology 111, N.Y. Acad. Press. 879, 1957) on tissue samples held in the anoxic state for a period of 90 minutes.

The results of these tests show that the administration of L-carnitine alpha-ketoglutarate is capable of affording much more marked protection than either L-carnitine or alpha-ketoglutaric acid alone against the lowering of ATP concentrations in papillary muscle caused by anoxia.

The protection afforded by L-carnitine alpha-ketoglutarate also proved to be unexpectedly greater than the sum of the effects of L-carnitine and alpha-ketoglutaric acid alone.

Whereas, in fact, in the untreated controls, the hypoxia reduced the ATP concentrations (mol/g tissue) from 1.70±0.68 to 0.46±0.071, in the rats treated with L-carnitine alpha-ketoglutarate the ATP concentrations were reduced to only 1.48±0.72. In the rats treated with L-carnitine or with alpha-ketoglutaric acid, the ATP concentrations were 0.59±0.31 and 0.75±0.80, respectively, whereas with the combination of the two compounds the concentration was 0.91±0.64.

Presentation forms of the compositions of the present invention include tablets, chewable tablets, pills, troches, lozenges, capsules, powders, granulates, phials, solutions, elixirs or drops.

In unit dosage form, the compositions comprise an amount of a ketoglutarate of L-carnitine or alkanoyl L-carnitine corresponding to about 50-1000 mg, preferably about 100-500 mg, of L-carnitine or alkanoyl L-carnitine as inner salts.

By way of example, one of such a composition comprises

| | | |
|---|---|---|
| L-carnitine alpha-ketoglutarate | mg | 500 |
| Cocarboxylase | mg | 2 |
| Vit. $B_6$ | mg | 5 |
| Vit. E | mg | 5 |
| Vit. PP | mg | 20 |
| Vit. C | mg | 50 |
| Coenzyme $Q_{10}$ | mg | 25 |
| Selenomethionine | µg | 50 |
| Magnesium | mg | 25 |
| Calcium | mg | 25 |
| Zinc | mg | 3 |

A mixture of L-carnitine alpha-ketoglutarate with one or more alkanoyl L-carnitine alpha-ketoglutarate may suitably substitute for L-carnitine alpha-ketoglutarate alone; for example (with reference to the previous composition):

| | | |
|---|---|---|
| L-carnitine alpha-ketoglutarate | mg | 200 |
| Acetyl L-carnitine alpha-ketoglutarate | mg | 200 |
| Propionyl L-carnitine alpha-ketoglutarate | mg | 200 |

The present invention also relates to the use of the aforesaid alpha-ketoglutarate for preparing an orally, parenterally or sublingually administrable composition for the prevention or treatment of organic or tissue disorders brought about by anoxia or inadequate energy supply or metabolic dysfunctions such as those occurring during strenuous physical exercise, in post-infarction states, cardiopathies or neuropathies, in subjects suffering from phenylketonuria and in chronic uremic patients undergoing regular haemodialytic treatment.

What is claimed is:

1. An alpha-ketoglutarate salt of L-carnitine or a lower alkanoyl L-carnitine in a ratio of one part lower alkanoyl L-carnitine to one part alpha-ketoglutaric anion and of the formula

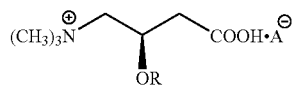

wherein:

A⁻ is the alpha-ketoglutarate anion; and

R is hydrogen or a straight- or branched-chain lower alkanoyl having 2-5 carbon atoms.

2. The alpha-ketoglutarate of claim 1, wherein R is an alkanoyl selected from the group consisting of acetyl, propionyl, valeryl and isovaleryl.

3. L-carnitine alpha-ketoglutarate.

4. Acetyl L-carnitine alpha-ketoglutarate.

5. Propionyl L-carnitine alpha-ketoglutarate.

6. Valeryl L-carnitine alpha-ketoglutarate.

7. Isovaleryl L-carnitine alpha-ketoglutarate.

8. A pharmaceutical composition comprising:

(a) an effective amount of a compound of claim 1; and (b) a pharmacologically acceptable excipient.

9. The composition of claim 8, wherein the alpha-ketoglutarate is selected from the group consisting of:

L-carnitine alpha-ketoglutarate;

acetyl L-carnitine alpha-ketoglutarate;

propionlyl L-carnitine alpha-ketoglutarate;

valeryl L-carnitine alpha-ketoglutarate; and isovaleryl L-carnitine alpha-ketoglutarate.

* * * * *